United States Patent

Kiesele et al.

[11] Patent Number: 5,865,973
[45] Date of Patent: Feb. 2, 1999

[54] ELECTROCHEMICAL MEASURING CELL

[75] Inventors: Herbert Kiesele; Frank Mett, both of Lübeck, Germany

[73] Assignee: Drägerwerk Aktiengesellschaft, Lübeck, Germany

[21] Appl. No.: 867,667

[22] Filed: Jun. 2, 1997

[30] Foreign Application Priority Data

Jun. 7, 1996 [DE] Germany ............... 196 22 930.8

[51] Int. Cl.6 ................................................ G01N 27/404
[52] U.S. Cl. .................... 204/415; 204/412; 205/783; 205/786.5
[58] Field of Search .................... 204/412, 415; 205/782.5, 783, 786.5

[56] References Cited

U.S. PATENT DOCUMENTS

| 3,380,905 | 4/1968 | Clark ............................ 204/415 |
| 4,152,233 | 5/1979 | Chand ........................... 204/415 |
| 4,578,157 | 3/1986 | Hitamura et al. ............... 204/415 |
| 4,908,105 | 3/1990 | Garner .......................... 204/415 |
| 5,298,146 | 3/1994 | Braden et al. ................. 204/415 |

*Primary Examiner*—T. Tung
*Attorney, Agent, or Firm*—Walter Ottesen

[57] ABSTRACT

The invention is directed to an electrochemical measuring cell to detect different gas components. The measuring cell includes several measuring electrodes (12, 15, 18) and a counter electrode 30 in an aqueous electrolyte 3. The measuring cell is improved with respect to the selectivity of the detection of the different gaseous components. A step-like offset 34 is provided between one of the measuring electrodes 12 and another measuring electrode 15.

7 Claims, 2 Drawing Sheets

ELECTROCHEMICAL MEASURING CELL

FIELD OF THE INVENTION

The invention relates to an electrochemical measuring cell for detecting gas components of a gas sample and includes several measuring or working electrodes and a counter electrode within an electrolyte. A diffusion membrane delimits the access of the gas to the working electrodes.

BACKGROUND OF THE INVENTION

A device for simultaneously detecting different gas components is disclosed in U.S. Pat. No. 5,298,146. This device includes a multiplicity of working electrodes, a common counter electrode and a common reference electrode within an aqueous electrolyte. The working electrodes are mounted segment-like behind a planar diffusion membrane and are subjected to the gas components to be detected via individual orifices which limit the entry of the gas. The orifices are mounted forward of the diffusion membrane. The formation of the measurement value takes place with the aid of a potentiostatic evaluation circuit which selects and controls the potentials at the working electrodes.

It is a disadvantage of this known device that all gas components diffuse through the diffusion membrane and, in this way, can reach all measuring electrodes. This leads especially to incorrect measurements when the entry to the measuring electrode for a gas component must be delimited by a diffusion barrier and/or by a selective filter. The diffusion barrier can, for example, be used when measuring oxygen. A further disadvantage is that the projection surface at the gas side can be utilized only incompletely because insulating intermediate spaces must remain between the electrodes. This is especially the case when trace gases are to be detected. A further disadvantage is that the fixing and insulation of contact leads is complex for a coplanar measuring electrode arrangement.

SUMMARY OF THE INVENTION

It is an object of the invention to provide a measuring cell of the kind described above wherein incorrect measurements because of cross-diffusion are prevented.

The electrochemical measuring cell of the invention is for detecting gas components of a gas sample and includes: a housing having an opening directed toward the gas sample and defining an electrolyte chamber; an electrolyte contained in the chamber; a plurality of measuring electrodes and a counter electrode disposed in the chamber so that the counter electrode is in spaced relationship to the measuring electrodes; a diffusion membrane interposed between the measuring electrodes and the opening for limiting access of the gas sample to the measuring electrodes; and, means for holding a first one of the measuring electrodes in stepped relationship to a second one of the measuring electrodes.

The advantage of the invention is seen in that a cross diffusion of gases to be detected is effectively prevented between individual working electrodes. This advantage is achieved by the arrangement of the measuring or working electrodes on different planes which are mutually parallel and offset relative to each other. Because of the height offset between the working electrodes, the electrode surface of the working electrodes, which is necessary for detecting the components, is optimally utilized. Corresponding gaps between the working electrodes would have to be provided in order to preclude cross-diffusion if the working electrodes would be arranged on a planar surface. In this way, the electrochemically effective surfaces of the working electrodes are however reduced. On the other hand, the diameter of the measuring cell would have to be increased for constant electrode surfaces. This situation can lead to assembly problems. In the electrochemical measuring cell of the invention, the longitudinal extension of the measuring cell is utilized for gap formation, which is generally not subjected to any limitations.

According to a feature of the invention, the diffusion membrane is subdivided into individual membrane segments which are assigned to corresponding working electrodes. The membrane segments together with the working electrodes are mounted so as to be parallel and offset to each other.

In an advantageous manner, an electrode holder has support surfaces which are offset with respect to each other in a step-like manner. The working electrodes with the corresponding membrane segments are attached to corresponding ones of these support surfaces. The electrode holder has a radially extending transverse strut on which the contact leads running to the working electrodes can be attached.

In an advantageous manner, the $O_2$ working electrode can be configured to have a circular surface. The remaining working electrodes are segments of a circular, annular element which can be arranged concentrically on different planes. These can also be arranged on a common diffusion membrane as long as no disturbing cross diffusion is expected between two working electrodes.

The measuring cell of the invention is especially advantageous for simultaneously detecting oxygen, carbon monoxide and/or hydrogen sulfide.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
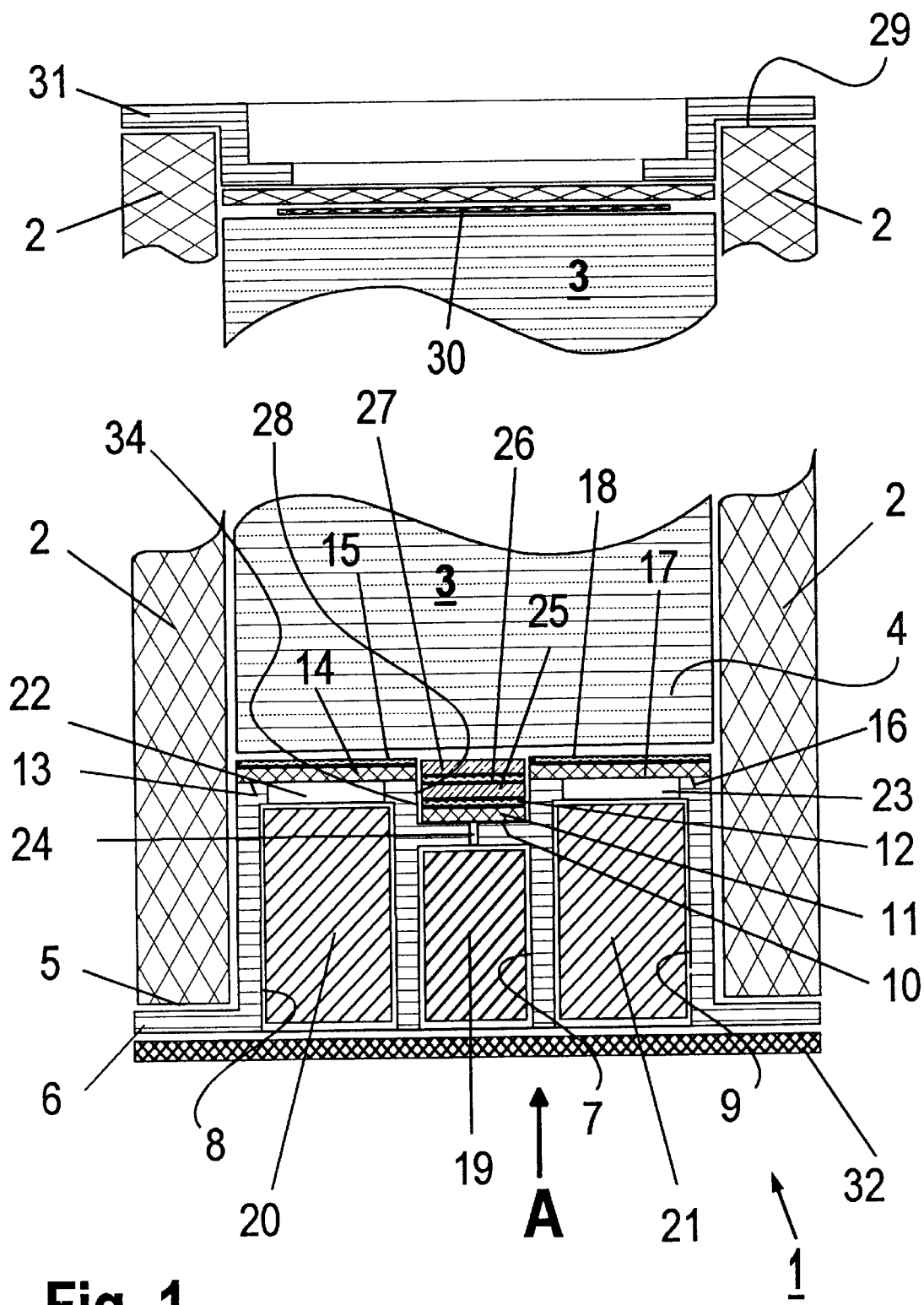
FIG. 1 is a side elevation view, in longitudinal section, of an electrochemical measuring cell according to the invention; and, FIG. 2 is a plan view of an electrode holder viewed in the direction of arrow A of FIG. 1.

FIG. 1 shows an electrochemical measuring cell 1 wherein a measuring cell housing 2 encloses an electrolyte space 4 filled with an aqueous electrolyte 3. The measuring cell 1 of the invention functions to simultaneously detect oxygen, carbon monoxide and hydrogen sulfide. An electrode holder 6 is arranged at a first end 5 of the measuring cell housing 2. The electrode holder 6 can preferably be made of polypropylene (PP) or polyethylene (PE). The electrode holder 6 has a first gas channel 7 for the detection of oxygen, a second gas channel 8 for the detection of carbon monoxide and a third gas channel 9 for the detection of hydrogen sulfide. The end of the electrode holder 6 facing toward the electrolyte space 4 is configured to have a first support surface 10 for attaching a first membrane segment 11 having an $O_2$ working electrode 12. The support surface 10 is located in the region of the first gas channel 7.

In a corresponding manner, a second support surface 13 is provided in the region of the second gas channel 8. The support surface 13 is for a second membrane segment 14 having a CO working electrode 15. A third support surface 16 is provided in the region of the third gas channel 9 and is provided for a third membrane segment 17 having a $H_2S$ work electrode 18. The gas channels (7, 8, 9) are provided with gas-selective filters (19, 20, 21), respectively. These filters hold back those gases which would lead to erroneous measurements at the corresponding working electrodes. The filters can, for example, be made of active charcoal for adsorption and are commercially available, for example, from Drägerwerk AG of Lübeck, Germany.

The gaseous components reach the corresponding working electrodes (15, 18) via respective orifices (22, 23). A diffusion capillary 24 delimits the entry of $O_2$ molecules to the $O_2$ working electrode 12.

A sandwich-like assembly is disposed rearward of the $O_2$ working electrode 12 and includes an electrolyte-permeable first nonwoven fabric 25, an $O_2$ protective electrode 26 and a second nonwoven fabric 27 which is likewise permeable to the electrolyte. The first membrane segment 11, the $O_2$ working electrode 12, the nonwoven fabrics (25, 27) and the $O_2$ protective electrode 26 are attached in a cup-shaped recess 28 within the electrode holder 6. The base of the recess 28 is the first support surface 10 having the diffusion capillary 24. A second end face 29 of the measuring cell housing 2 is disposed opposite the first end face 5 and is closed by a holder 31 for a counter electrode 30. The gas-selective filters (19, 20, 21) forward of the corresponding working electrodes (12, 15, 18) are covered by a dust filter 32. For conducting the measurement, the electrodes (12, 15, 18, 26, 30) are connected to a potentiostat (not shown) in a manner known per se.

A cross diffusion of oxygen between the $O_2$ working electrode 12 and the working electrodes (15, 18) is prevented because of the step-like recess 34 between the first support surface 10 and the second and third support surfaces 13 and 16. Cross diffusion between the membrane segments (14, 17) is also not possible because of the segment-like diffusion membrane. An erroneous measurement of oxygen is prevented because of the suppression of the cross diffusion.

Figure 2:
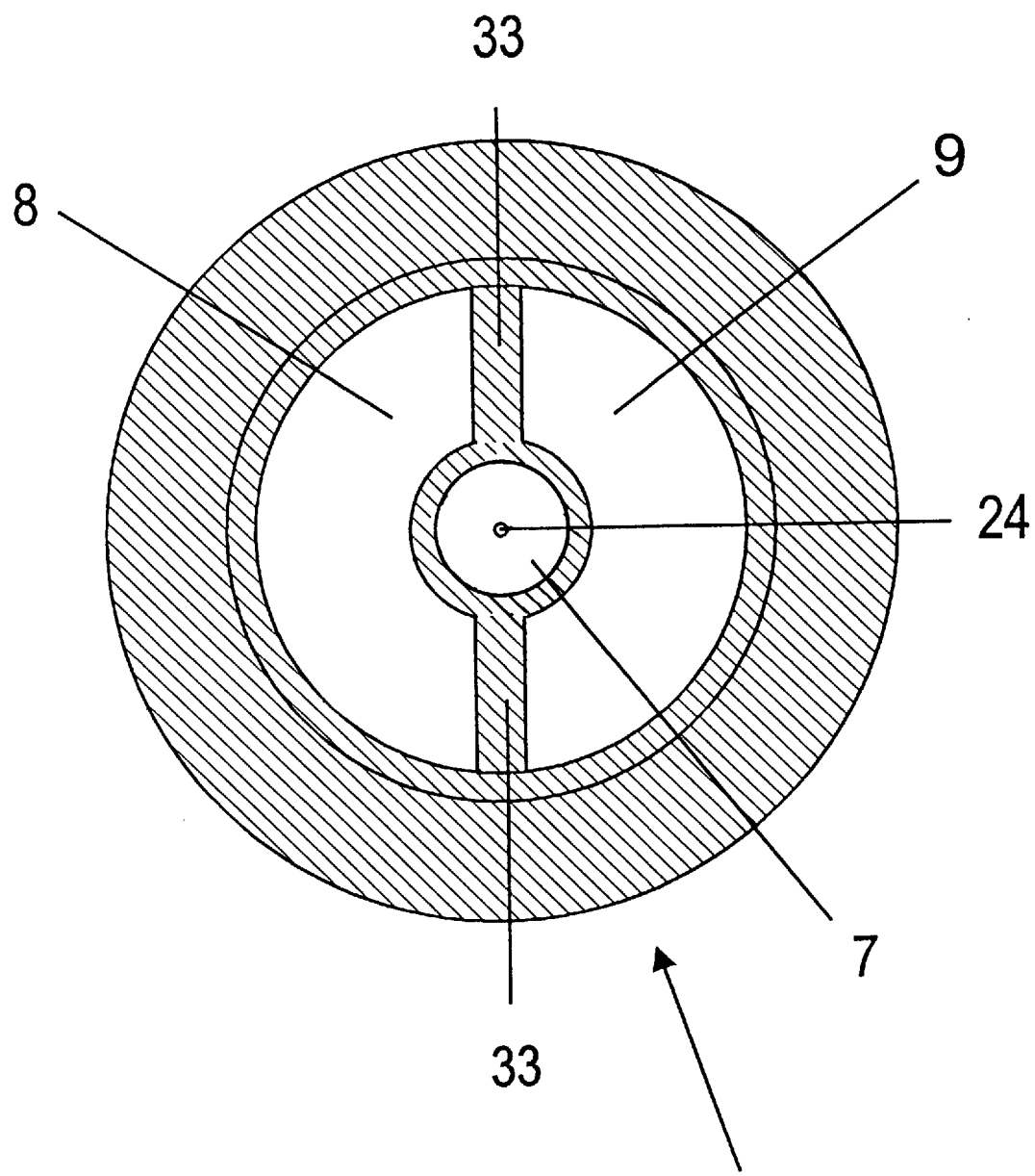

FIG. 2 shows a plan view of the electrode holder 6 viewed in the direction of arrow A of FIG. 1 with filter 32 as well as filters (19, 20, 21) removed. The gas channels (8, 9) and the working electrodes (15, 18) are configured in the form of sectors and are separated from each other by a radially-extending transverse strut 33. The transverse strut 33 facilitates attachment of contact leads (not shown) which lead to the electrodes (12, 26) and the membrane segments (14, 17).

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting a plurality of different gas components of a gas sample, the electrochemical measuring cell comprising:

a housing having a plurality of openings directed toward the gas sample and defining an electrolyte chamber;

an electrolyte contained in said chamber;

a plurality of measuring electrodes and a counter electrode disposed in said chamber so that said counter electrode is in spaced relationship to said measuring electrodes;

a plurality of diffusion membrane segments interposed between said measuring electrodes and said openings, respectively, and being assigned to respective ones of said measuring electrodes for limiting access of corresponding selected ones of said gas components to said measuring electrodes; and, means for holding a first one of said measuring electrodes and a first one of said membrane segments in stepped relationship to a second one of said measuring electrodes and a second one of said membrane segments so that each membrane segment and the measuring electrode corresponding thereto is offset with respect to at least a selected one of the remaining membrane segments and the measuring electrode corresponding thereto.

2. The electrochemical measuring cell of claim 1, said diffusion membrane segments being separate from each other thereby preventing cross diffusion between said diffusion membrane segments; and, each of said measuring electrodes being mounted directly on the diffusion membrane segment corresponding thereto so as to make the diffusion path the same between each of said measuring electrodes and the diffusion membrane segment corresponding thereto.

3. The electrochemical measuring cell of claim 2, said holding means including an electrode holder having a plurality of support surfaces corresponding to respective ones of said measuring electrodes; at least one of said support surfaces being in stepped spaced relationship to the remainder of said support surfaces; and, said support surfaces being configured to attach corresponding ones of said measuring electrodes and diffusion membrane segments thereto.

4. The electrochemical measuring cell of claim 3, said electrode holder comprising a body having a plurality of channels formed therein and leading to respective ones of said measuring electrodes; and, at least one transverse strut extending radially in said body between at least two of said channels.

5. The electrochemical measuring cell of claim 4, wherein said gas components to be detected include oxygen, carbon monoxide and hydrogen sulfide; and, wherein said electrochemical measuring cell further comprises a plurality of filters disposed in respective ones of said channels and each of said filters being adapted to pass one of said gas components while holding back other ones of said gas components.

6. The electrochemical measuring cell of claim 4, further comprising a plurality of filters disposed in respective ones of said channels and each of said filters being adapted to pass one of said gas components to a corresponding one of said measuring electrodes.

7. The electrochemical measuring cell of claim 3, one of said measuring electrodes being an oxygen measuring electrode and having a surface delimited by a circular periphery; and, each of the remaining ones of said measuring electrodes having a shape corresponding to an annular segment.

* * * * *